US006753173B1

(12) United States Patent
Gokhale et al.

(10) Patent No.: US 6,753,173 B1
(45) Date of Patent: Jun. 22, 2004

(54) METHODS TO MEDIATE POLYKETIDE SYNTHASE MODULE EFFECTIVENESS

(75) Inventors: Rajesh S. Gokhale, Delhi (IN); Stuart Tsuji, Stanford, CA (US); Chaitan Khosla, Palo Alto, CA (US)

(73) Assignee: Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 09/500,747

(22) Filed: Feb. 9, 2000

Related U.S. Application Data

(60) Provisional application No. 60/119,363, filed on Feb. 9, 1999.

(51) Int. Cl.[7] .................................................. C12N 9/00
(52) U.S. Cl. ...................................................... 435/183
(58) Field of Search ........................................ 435/183

(56) References Cited

U.S. PATENT DOCUMENTS

| | | | |
|---|---|---|---|
| 4,551,433 A | 11/1985 | DeBoer ...................... 435/253 |
| 4,874,748 A | 10/1989 | Katz et al. ..................... 514/29 |
| 4,935,340 A | 6/1990 | Baltz et al. | |
| 5,063,155 A | 11/1991 | Cox et al. ...................... 435/76 |
| 5,098,837 A | 3/1992 | Beckmann et al. ....... 435/172.3 |
| 5,149,639 A | 9/1992 | Katz et al. ..................... 435/76 |
| 5,168,052 A | 12/1992 | Cox et al. ...................... 435/72 |
| 5,252,474 A | 10/1993 | Gewain et al. .......... 435/172.3 |
| 5,475,099 A | 12/1995 | Knauf et al. | |
| 5,514,544 A | 5/1996 | Rao et al. ....................... 435/6 |
| 5,672,491 A | 9/1997 | Khosla et al. .............. 435/148 |
| 5,712,146 A | 1/1998 | Khosla et al. ......... 435/252.35 |
| 5,824,513 A | 10/1998 | Katz et al. ..................... 435/76 |
| 5,830,750 A | 11/1998 | Khosla et al. ......... 435/252.35 |
| 5,843,718 A | 12/1998 | Khosla et al. ............. 435/69.1 |
| 6,004,787 A | 12/1999 | Katz et al. ................... 435/183 |
| 6,060,234 A | 5/2000 | Katz et al. ..................... 435/4 |
| 6,063,561 A | 5/2000 | Katz et al. ..................... 435/4 |
| 6,066,721 A | 5/2000 | Khosla et al. | |
| 6,080,555 A | 6/2000 | Khosla et al. | |
| 6,200,813 B1 | 3/2001 | Katz et al. ................... 435/477 |
| 6,271,255 B1 | 8/2001 | Leadlay et al. ............. 514/450 |

FOREIGN PATENT DOCUMENTS

| | | |
|---|---|---|
| WO | WO 93/13663 | 7/1993 |
| WO | WO 95/08548 | 3/1995 |
| WO | WO 96/40968 | 12/1996 |
| WO | WO 97/02358 | 1/1997 |
| WO | WO 97/14789 | 4/1997 |
| WO | WO 98/01546 | 1/1998 |
| WO | WO 98/01571 | 1/1998 |
| WO | WO 98/27203 | 6/1998 |
| WO | WO 98/49315 | 11/1998 |
| WO | WO 98/54308 | 12/1998 |

OTHER PUBLICATIONS

Tang et al. Formation of functional heterologous complexes using subunits form the picromycin, erthroymycin, and oleandomycin polyketide synthases. Chem. Biol. (2000) 7:77–84.*
Aparicio et al., J. of Biol. Chem. (1994) 269(11):8524–8528.
Bartel et al., J. Bacteriol. (1990) 172(9):4816–4826.
Beck et al., Eur. J. Biochem. (1990) 192:487–498.
Bedford et al., Chemistry & Biology (1996) 3(10):827–831.
Bevitt et al., Eur. J. Biochem. (1992) 204:39–49.
Bibb et al., EMBO J. (1989) 8(9):2727–2736.
Brown et al., J. Chem. Soc. Chem. Commun. (1995) 15:1517–1518.
Caballero et al., Mol. Gen. Genet. (1991) 230:401–412.
Caffrey et al., Eur. J. Biochem. (1991) 195:823–830.
Caffrey et al., FEBS Lett. (1992) 304:225–228.
Cane et al., J. Am. Chem. Soc. (1993) 115:522–526.
Cane et al., J. Antibiotics (1995) 48:647–651.
Corcoran et al., in 5th International Congress of Chemotherapy, Vienna, Abstracts of Communications (1967) pp. 35–40.
Corcoran, ed., in Antibiotics Volume IV Biosynthesis, Springer–Verlag, New York (1982) pp. 145–150.
Cortes et al. Nature (1990) 348:176–178.
Dalbie–McFarland et al., Proc. Natl. Acad. Sci. USA (1982) 79:6409–6413.
Davis et al., Abst. of the Genetics of Industrial Microorganisms Mtg. (1994) P288:192.
Dimroth et al., Eur. J. Biochem. (1970) 13:98–110 non–English.
Donadio et al., Gene (1992) 111:51–60.
Donadio et al., Gene (1992) 115:97–103.
Donadio et al., Industrial Microorganism, Basic and Applied Molecular Genetics, R. H. Baltz, G. D. Hegeman and PIL. Skatrud (eds) (Amer. Soc. Microbiol.), Washington, D.C. (1993) pp. 251–265.
Donadio et al., Proc. Natl. Acad. Sci. USA (1993) 90:7119–7123.
Donadio et al., Science (1991) 252:675–679.
Evans et al., J. Am. Chem. Soc. (1992) 114:9434–9453.
Fernandez–Moreno et al., Cell (1991) 66:769–780.
Fernandez–Moreno et al., J. Biol. Chem. (1992) 267:19278–19390.
Floss et al. Tetrahydron (1991) 47(31):6045–6058.
Geisselsoder et al., BioTechniques (1987) 5:786–791.
Gordon et al., Acc. Chem. Res. (1996) 29(3):144–154.

(List continued on next page.)

Primary Examiner—Ponnathapu Achutamurthy
Assistant Examiner—Kathleen Kerr
(74) Attorney, Agent, or Firm—Morrison & Foerster LLP

(57) ABSTRACT

Linking sequences that modulate cross-talk between modules of Type I polyketide synthases have been identified and methods for their use are described. Arbitrarily chosen modules can be mixed and matched by supplying the appropriate linkers to facilitate transfer of a growing polyketide chain between modules. Employing these techniques, new polyketide end products may be obtained.

28 Claims, 3 Drawing Sheets

OTHER PUBLICATIONS

Hallam, Gene (1988) 74:305–320.
Hamilton et al., J. Bacteriol. (1989) 171:4617–4622.
Hershberger et al. (1989) "Genetics and Molecular Biology of Industrial Microorganisms," Am. Soc. for Microbiol. (Washington, DC) pp. 68–84.
Hopwood et al., Nature (1985) 314(6012):642–644.
Hopwood et al., Phil. Trans. R. Soc. Lond. B (1989) 324:549–562.
Hopwood et al., Secondary Metaboiltes: Their Function and Evolution (1992) Wiley Chichester (Ciba Foundation Symposium 171) pp. 88–112.
Hunaitit et al., Antimicrobial Agents and Chemotherapy (1984) 25(2):173–178.
Hutchinson, Bio/Technology (1994) 12:375–380.
Ireland et al., J. Org. Chem. (1980) 45:1868–1880.
Jay et al., J. Biol. Chem. (1984) 259:6311–6317.
Kao et al., J. Am. Chem. Soc. (1994) 16:11612–11613.
Kao et al., J. Am. Chem. Soc. (1995) 117(35):9105–9106.
Kao et al., J. Am. Chem. Soc. (1996) 118(38):9184–9185.
Kao et al., J. Am. Chem. Soc. (1997) 119(46):1139–11340.
Katz et al., Ann. Review Microbiol. (1993) 47:875–912.
Khosla et al., J. Bacteriol. (1993) 175:2197–2204.
Khosla et al., Molec. Microbiol. (1992) 6(12):3237–3249.
Kramer et al., J. Am. Chem. Soc. (1997) 119(4):635–639
Kuhstoss et al., Gene (1996) 183:231–236.
Kunkel, Proc. Natl. Acad. Sci. USA (1985) 82:488–492.
Lambalot et al., J. Antibiotics (1992) 45:1981–1982.
Lanz et al., J. of Biol. Chem. (1991) 266(15):9971–9976.
Leadlay et al., Biochem. Soc. Transactions (1993) 21:218–222.
Lehrer et al., J. Immun. Meth. (1991) 137:167–173.
MacNeil, J. Bacteriol. (1988) 170:5607–5612.
MacNeil et al., Gene (1992) 115:119–125.
Malpartida et al., Nature (1984) 309:462–464.
Malpartida et al., Mol. Gen Genet. (1986) 205:66–73.
Malpartida et al., Nature (1987) 325(6107):818–821.
Marsden et al., Science (1994) 263:378–380.
Marsden et al., Science (1998) 279:199–202.
Martin et al., J. Am. Chem. Soc. (1997) 119:3193–3194.
Masamune et al., J. Am. Chem. Soc. (1975) 97:3512–3513.
Masumoto et al., Tetrohedron Lett. (1988) 29:3575–3578.
McAlpine et al., The Journal of Antibiotics (1987) 40(8):1115–1122.
Oliynyk et al., Chem. and Biol. (1996) 3:833–839.
Omura et al., J. Biochem. (1974) 75:193–195.
Perun, Drug Action and Drug Resistance in Bacteria, vol. 1, S. Mitsuhashi (ed.) Univ. Park Press, Baltimore, 1977.
Roberts et al., FEBS Lett. (1983) 159(1,2):13–16.
Roberts et al. Biochem. Soc. Transactions (1984) 12:642–643.
Roberts et al., Biochem. Soc. Transactions (1992) 21:325.
Roberts et al., Eur. J. Biochem. (1993) 214:305–311.
Robinson, Phil. Trans. R. Soc. Lond. B (1991) 332:107–114.
Ruan et al., J. of Bacteriology (1997) 79(20):6416–6425.
Rudd et al., J. Gen. Microbiol. (1979) 114:35–43.

Shen et al., Science (1993) 262:1535–1540.
Sherman et al., J. Bacteriol. (1992) 174:6184–6190.
Sherman et al., EMBO J. (1989) 8:2717–2725.
Spencer et al., Biochem. J. (1992) 288;839–846.
Strohl et al., Molecular Microbiology (1992) 6(2):147–152.
Strohl et al., Society of Industrial Microbiology (1991) 7:163–174.
Toshima et al., J. Am. Chem. Soc. (1995) 117:3717–3727.
Tsoi et al., Chemistry & Biology (1985) 2:355–362.
Tuan et al., Gene (1990) 90:21–29.
Vedejs et al., J. Am. Chem. Soc. (1987) 109:5437–5446.
Vedejs et al., J. Am. Chem. Soc. (1989) 111:8430–8438.
Wawszkiewicz et al., Biochemische Zeitscrift (1964) 340:213–227.
Wiseman et al., Chemistry & Biology (1995) 2(9):583–589.
Fu et al., "Engineered Biosynthesis of Novel Polyketides: Stereochemical Course ot Two Reactions Catalyzed by a Polyketide Synthase," Biochemistry (1994) 33:9321–9326.
Kao et al., "Engineered Biosynthesis of a Complete Macrolactone in a Heterologous Host," Science (1994) 265:509–512.
Khosla, "Harnessing the Biosynthetic Potential of Modular Polyketide Synthases," Chem Rev (1997) 97:2577–2590.
Khosla et al., "Generation of Polyketide Libraries Via Combinatorial Biosynthesis," Trends Biotechnol (1996) 14(9):335–341.
McDaniel et al., "Engineered Biosynthesis of Novel Polyketides," Science (1993) 262:1546–1550.
Ranganathan et al., "Knowledge-based Design of Bimodular and Trimodular Polyketide Synthases Based on Domain and Module Swaps: A Route to Simple Statin Analogues," Chem & Biol. (1999) 6:731–741.
Rohr, "Combinatorial Biosynthesis—An Approach in the Near Future?, " Angew Chem Int Ed Engl (1995) 34(8):881–888.
Staunton et al., "Biosynthesis of Erythromycin and Rapamycin," Chem Rev (1997) 97:2611–2629.
Aparicio, J et al. (1996). Gene 169:9–16.
Bohm, I. et al. (1998). Chem. & Biol 5:407–412.
Gokhale, R. et al., (1998). Biochemistry 37:2524–2528 (abstract).
Gokhale, R. et al. (1999) Science 284:482–485.
Kao, K. et al., (1996). Biochemistry 35:12363–12368.
Lau, J. et al. (1999). Biochemistry 38:1643–1651.
Pieper, R. et al., (1997). Biochemistry 36:1846–1851 (abstract).
Sanz, J.M. et al. (1996). Eur J Biochem 235:601–605 (abstract).
Staunton, J. et al. (1996). Nat Struct Biol 3:188–192.
Bao, W. et al. (1998) Biochemistry 37(22):8132–8138.
Bedford, D. et al. (1996). Chem & Biol 3(10):827–831.
Kakavas, S. et al. (1997). J. of Bacteriology 179(23):7515–7522.
McDaniel, R. et al. (1997). Chem & Biol 4(9):667–674.

* cited by examiner

(a) INTRA-POLYPEPTIDE LINKER

```
M2ery:   GGATGAEQAAPATT..APVD          (SEQ ID NO:3)
M4ery:   VGDAD..QAA.VRVVGAA.DES        (SEQ ID NO:4)
M6ery:   VGAAEAEQA.PALVREVPKDAD        (SEQ ID NO:5)
M2rif:   FGSA.A.NR.PAEIGTAAAE          (SEQ ID NO:6)
M3rif:   IG..ER.PAAPAPVTRDVSD          (SEQ ID NO:7)
M5rif:   GETVAGAPATPVTTVADAG           (SEQ ID NO:8)
M3rap:   .ELFTGENPAPVRGPVSAVGQD        (SEQ ID NO:9)
M4rap:   .ELFTGENPAPVRGPVSVVGQD        (SEQ ID NO:10)
M7rap:   .ELFTGENPAPVRGPVSA.GQD        (SEQ ID NO:11)
```

(b) N-TERMINAL INTER-POLYPEPTIDE LINKER

```
M3ery:   ......VTD SE KVAEYLRR .ATLDLRAAR QRIRE..LES            (SEQ ID NO:12)
M5ery:   MSGDNGM.TE E.KLRRYLKR TVT.ELDSVT ARLRE..VEH RAG        (SEQ ID NO:13)
M4rif:   ......MSAPNE QIVDAL.R ASLKE....N VRLQQENSAL AAAAA      (SEQ ID NO:14)
M7rif:   ......VSASYE KVVEAL.R KSLEE....V GTLKKRNRQL ADAAG      (SEQ ID NO:15)
M8rif:   ........V.AD EGQLRDYLKR .AIADARDAR TRLRE..VEE QAR      (SEQ ID NO:16)
M9rif:   ........MATD E.KLLKYLKR .VTAELHS.. ..LRKQGARH .AD      (SEQ ID NO:17)
M5rap:   ......MR.. EDQLLDAL.R KSVKE....N ARLRKANTSL RAAMD      (SEQ ID NO:18)
M11rap:  ......M.PEQD KVVEYL.R WATAELHTTR AKL......EA LAAANT    (SEQ ID NO:19)
```

FIGURE 3

METHODS TO MEDIATE POLYKETIDE SYNTHASE MODULE EFFECTIVENESS

This application claims priority under 35 U.S.C. § 119(e) from provisional application No. 60/119,363 filed 9 Feb. 1999, the contents of which are incorporated herein by reference.

The invention herein was made, at least in part, based on support by grants from the National Institutes of Health, CA-66736 and GM-22172 and from the, National Science Foundation, BES-9806774. The U.S. government has certain rights in this invention.

TECHNICAL FIELD

The invention is directed to facilitating usage by polyketide synthase modules of nascent polyketide chains. More specifically, the invention concerns including inter-module and intramnodule linkers in constructions for synthesis of desired polyketides.

BACKGROUND OF THE INVENTION

Polyketides are a class of compounds synthesized from 2-carbon units through a series of condensations and subsequent modifications. Polyketides occur in many types of organisms, including fungi and mycelial bacteria, in particular, the actinomycetes. Polyketides are biologically active molecules with a wide variety of structures, and the class encompasses numerous compounds with diverse activities. Tetracycline, erythromycin, epothilone, FK-506, FK-520, narbomycin, picromycin, rapamycin, spinocyn, and tylosin are examples of polyketides. Given the difficulty in producing polyketide compounds by traditional chemical methodology, and the typically low production of polyketides in wild-type cells, there has been considerable interest in finding improved or alternate means to produce polyketide compounds.

The biosynthetic diversity of polyketides is generated by repetitive condensations of simple monomers by polyketide synthase (PKS) enzymes that mimic fatty acid synthases. For instance, the deoxyerythronolide-B synthase catalyzes the chain extension of a primer with several methylmalonyl coenzyme A (MeMalCoA) extender units to produce the erythromycin core.

The cloning, analysis, and recombinant DNA technology of genes that encode PKS enzymes allows one to manipulate a known PKS gene cluster either to produce the polyketide synthesized by that PKS at higher levels than occur in nature or in hosts that otherwise do not produce the polyketide. The technology also allows one to produce molecules that are structurally related to, but distinct from, the polyketides produced from known PKS gene clusters. See, e.g., PCT publication Nos. WO 93/13663; 95/08548; 96/40968; 97/02358; 98/27203; and 98/49315; U.S. Pat. Nos. 4,874, 748; 5,063,155; 5,098,837; 5,149,639; 5,672,491; 5,712, 146; 5,830,750; and 5,843,718; and Fu, et al., 1994, *Biochemistry* 33: 9321–9326; McDaniel, et al., 1993, *Science* 262: 1546–550; and Rohr, 1995, *Angew. Chem. Int. Ed. Engl.* 34(8): 881–888, each of which is incorporated herein by reference.

PKSs catalyze the biosynthesis of polyketides through repeated, decarboxylative Claisen condensations between acylthioester building blocks. The buildinhg blocks used to form complex polyketides are typically acylthioesters, such as acetyl, butyryl, propionyl, malonyl, hydroxymalonyl, methylmalonyl, and ethylmalonyl CoA. Two major types of PKS enzymes are known; these differ in their composition and mode of a synthesis of the polyketide synthesized. These two major types of PKS enzymes are commonly referred to as Type I or "modular" and Type II "iterative" PKS enzymes.

The present invention concerns modular PKS. In the Type I or modular PKS enzyme group, a set of separate catalytic active sites (each active site is termed a "domain", and a set thereof is termed a "module"exists for each cycle of carbon chain elongation and modification in the polyketide synthesis pathway. The typical modular PKS is composed of several large polypeptides, which can be segregated from amino to carboxy terminii into a loading module, multiple extender modules, and a releasing (or thioesterase) domain. The PKS enzyme known as 6-deoxyerythronolide B synthase (DEBS) is a typical Type I PKS. In DEBS, there is a loading module, six extender modules, and a thioesterase (TE) domain. The loading module, six extender modules, and TE of DEBS are present on three separate proteins (designated DEBS-1, DEBS-2, and DEBS-3, with two extender modules per protein). Each of the DEBS polypeptides is encoded by a separate open reading frame (ORF) or gene; these genes are known as eryAI, eryAII, and eryAIII. See FIG. 1. There is considerable interest in the genetic and chemical reprogramming of modular PKSs (see, e.g., Khosla, 1997, *Chem. Rev.* 97:2577–2590, and Staunton, et al., 1997, *Chem. Rev.* 2611–2629, each of which is; incorporated herein by reference).

Generally, the loading module is responsible for binding the first building block used to synthesize the polyketide and transferring it to the first extender module. The loading module of DEBS consists of an acyltransferase (AT) domain and an acyl carrier protein (ACP) domain. Another type of loading module utilizes an inactivated KS, an AT, and an ACP. This inactivated KS is in some instances called $KS^Q$, where the superscript letter is the abbreviation for the amino acid, glutamine, that is present instead of the active site cysteine required for ketosynthase activity. In other PKS enzymes, including the FK-520 PKS, the loading module incorporates an unusual starter unit and is composed of a CoA ligase activity domain. In any event, the loading module recognizes a particular acyl-CoA (usually acetyl or propionyl but sometimes butyryl) and transfers it as a thiol ester to the ACP of the loading module.

The AT on each of the extender modules recognizes a particular extender-CoA (malonyl or alpha-substituted malonyl, i.e., methylmalonyl, ethylmalonyl, and hydroxymalonyl) and transfers it to the ACP of that extender module to form a thioester. Each extender module is responsible for accepting a compound from a prior module, binding a building block, attaching the building block to the compound from the prior module, optionally performing one or more additional functions, and transferring the resulting compound to the next module. The transfer into a module is mediated by the KS domain which is upstream of the remaining catalytic domains. The additional functions are performed by enzymes which comprise a ketoreductase (Kg) which reduces the carbonyl group generated from the condensation to an alcohol, a dehydratase (DH) which converts the alcohol to a double bond, and an enoyl reductase (ER) which reduces the doublebond to a single bond. These catalytic domains appear to be immediately adjacent and not separated by any linking sequences. Collectively, they can be called "beta-carbonyl modifying" domains. Thus, a particular module may contain none of these activities, only KR, or KR+DH, or KR+DH+ER. Thus, the order of domains from the N-terminus of a particular module is KS, AT, beta-carbonyl modifying domains (if present), ACP. The order, N→C of the beta-carbonyl modifying enzymes is DH ER KR.

Thus, each extender module of a modular PKS contains zero, one, two, or three enzymes that modify the beta-carbon of the growing polyketide chain downstream of the AT catalytic domain. A typical (non-loading) minimal Type I PKS extender module is exemplified by extender module 3 of DEBS, which contains only a KS domain, an AT domain, and an ACP domain. The next extender module, module 4, contains all three 10 beta-carbonyl modifying enzymes. (The beta-carbonyl modifying enzymes effect such modification on the extender unit that has been added by the previous module.)

Once the PKS is primed with acyl- and malonyl-ACPs, the acyl group of the loading module migrates to form a thiol ester (trans-esterification) at the KS of the first extender module; at this stage, extender module one possesses an acyl-KS adjacent to a malonyl (or substituted malonyl) ACP. The acyl group derived from the loading module is then covalently attached to the alpha-carbon of the malonyl group to form a carbon-carbon bond, driven by concomitant decarboxylation, and generating a new acyl-ACP that has a backbone two carbons longer than the loading building block (elongation or extension).

After traversing the final extender module, the polyketide encounters a releasing domain that cleaves the polyketide from the PKS and typically cyclizes the polyketide.

For example, final synthesis of 6-dEB is regulated by a TE domain located at the end of extender module six. In the synthesis of 6dEB, the TE domain catalyzes cyclization of the macrolide ring by formation of an ester linkage. In FK-506, FK-520rapamycin, and similar polyketides, the ester linkage formed by the TE activity is replaced by a linkage formed by incorporation of a pipecolate acid residue. The enzymatic activity that catalyzes this incorporation for the raparnycin enzyme is known as RapP, encoded by the rapP gene. The polyketide can be modified further by tailoring enzymes, these enzymes add carbohydrate groups or methyl groups, or make other modifications, i.e., oxidation or reduction, on the polyketide core molecule. For example, 6-dEB is hydroxylated at C6 and C12 and glycosylated at C3 and C5 in the synthesis of erythromycin A.

In PKS polypeptides, the regions that encode enzymatic activities (domains) are separated by linker or "scaffold"-encoding regions. These scaffold regions encode amino acid sequences that space the domains at the appropriate distances and in the correct order. Thus, the linker regions of a PKS protein collectively can be considered to encode a scaffold into which the various domains (and thus modules) are placed in a particular order and spatial arrangement. Generally, this organization permits PKS catalytic domains of different or identical substrate specificities to be substituted (usually at the DNA level) between PKS enzymes by various available methodologies. Thus, there is considerable flexibility in the design of new PKS enzymes with the result that known polyketides can be produced more effectively, and novel polyketides useful as pharmaceuticals or for otherpurposes can be made.

PCT publication WO 98/49315, the contents of which are incorporated herein by reference, describes an approach for modifying the enzymatic activities included within modules of a PKS by maintaining the scaffolding intact but replacing catalytic domains with different: catalytic domains. U.S. Ser. No. 09/346,860 filed 2 Jul. 1999, now U.S. Pat. No. 6,221,641. and the corresponding PCT publication WO 00/01838, also filed on that date, and incorporated herein by reference describe alternative methods by altering the hypervariable region of the AT domains so as to alter the specificity for an extender unit and alteration of the KS domains to control stereochemistry. The present invention takes advantage of the approach of manipulating modules so that the catalytic activities of an entire module are placed in the appropriate sequence to construct a desired polyketide. The ability to utilize this approach depends on effecting an appropriate means for the module to incorporate a growing polyketide chain, which involves assuring that an appropriate linker region is included. Since the filing of the provisional application from which the present application claims priority, a related paper has been published by Ranganathan, A., et al., *Chem. & Biol.* (1999) 6:731–741. In this paper, intrapolypeptide linkages are fortuitously supplied to chimeric modules by including the KS region of the native downstream module in a chimera between the corresponding upstream module and the portions downstream of the KS domain in a heterologous module. Alternatively, the downstream module will include the ACP catalytic domain of the native upstream module fused to the remainder of a heterologous module upstream in the chimera.

DISCLOSURE OF THE INVENTION

The invention is directed to an efficient method for constructing an arbitrarily chosen polyketide synthase, and therefore a desired polyketide, by manipulating entire modules of Type I polyketide synthases. The invention enables this approach by providing the modules with the appropriate "lead-in" or linker sequence to the ketosynthase (KS). Applicants have discovered that the appropriate linker between modules is required upstream of the relevant KS in order to permit the module to accept the nascent polyketide chain, and, in the case of intermolecular transfer, appropriate pairing of N-terrninal and C-terminal regions assures the appropriate transfer. The nature of this linker varies depending on whether the module is covalently linked downstream from another module, or whether it forms the N-termninus of the polypeptide.

Thus, in one aspect, the invention is directed to a method to construct a functional polyketide synthase which method comprises providing each module contained in the desired polyketide synthase with an appropriate intrapolypeptide linker (RAL) when said module is downstream in the same polypeptide from a module derived from a different PKS and with an appropriate interpolypeptide linker (ERL) when the module is derived from a PKS where the module is the N-terminal module of a polypeptide. If the module at the N-terminus of a polypeptide is to accept a nascent polyketide chains from an upstream module, the interpolypeptide linker needs to include the appropriate amino acid sequence at the C-terminus of the module donating the nascent chain.

In describing a "module" being provided with linker(s) the term "module" refers to the functional portions extending approximately from the N-terminus 6f the KS catalytic region to the C-terminus of the ACP—i.e., excludes the linker portions otherwise considered a portion of the module.

As further described below, any order of modules of desired specificity can be assured by providing the appropriate linkers either intermolecularly or intramolecularly. Thus, the polyketide synthase can be assembled from individual modules by providing the appropriate linkers to assure that the polyketide chain will be passed in the correct sequence from one module to the next and by assembling these modules either by directly providing the polypeptides containing them or by co-expressing nucleotide sequences and coding them in a host cell.

In other aspects, the invention is directed to materials and compositions useful in carrying out the method, in particular to isolated DNA fragments which contain the appropriate intrapolypeptide and interpolypeptide linkers. The invention also relates to methods to construct functional polyketide synthases from libraries of modules and to polyketides prepared by supplying appropriate substrates to reconstructed polyketide synthases. The polyketides thus prepared can be "tailored" using either isolated enzymes or feeding the polyketides to an organism containing these enzymes to convert them to. anti-infectives or compounds of other activities such as motolides by such post-polyketide modifications as hydroxylation and glycosylation. The ketides or ketolides or their modified forms can also be further derivatized using chemical synthetic methods.

BRIEF DESCRIPTION OF THE DRAWINGS

FIG. 3 shows the structres of intrapolypeptide linkers and the N-terminal portions of interpolypeptide linkers (SEQ ID NOS:3–19) derived from various Type I PKS.

MODES OF CARRYING OUT THE INVENTION

Figure 1:
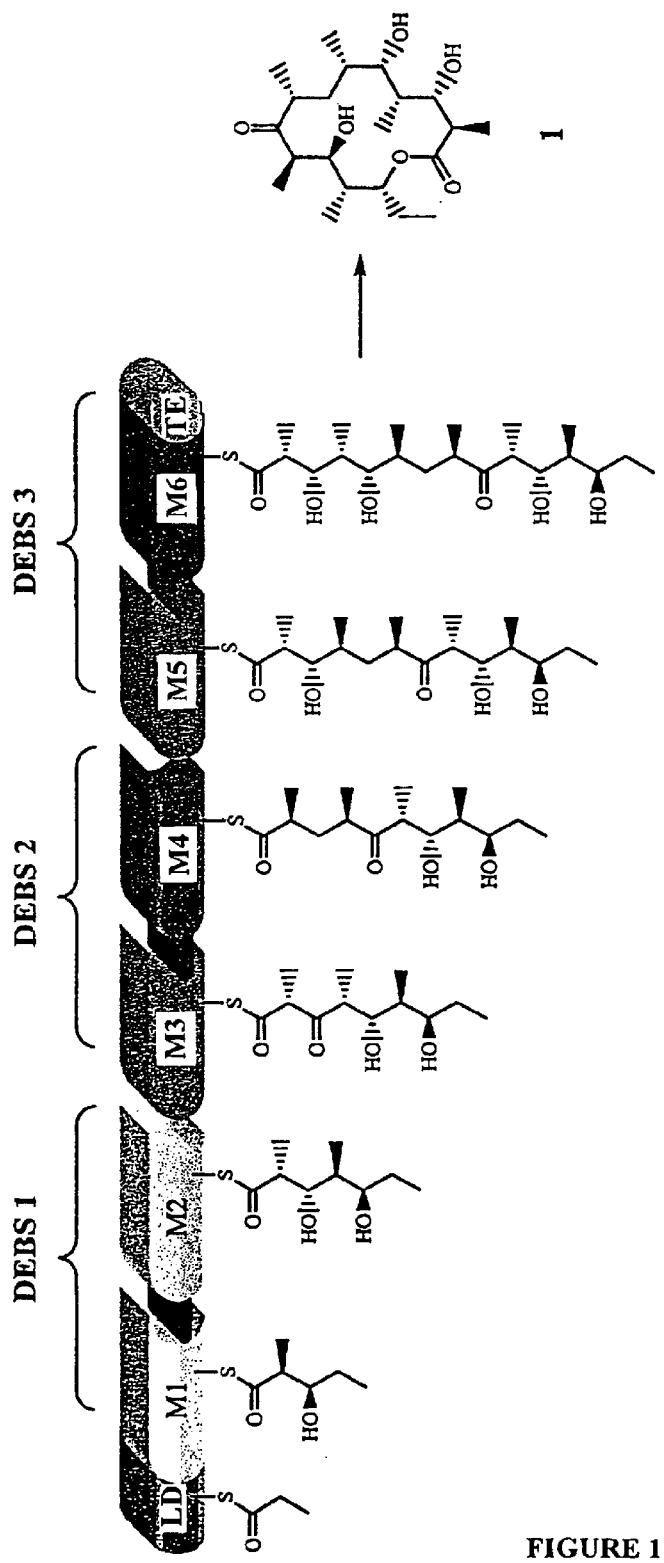
FIG. 1 is a diagram of the erythromycin PKS which forms 6-dEB, the core precursor of erythiromycin. As shown, the PKS is comprised of three proteins, DEBS-1, DEBS-2 and DEBS-3 which are encoded by three genes, commonly called eryAI, eryAII and eryAIII.

The invention takes advantage of the identification of the amino acid sequences for supplying an appropriate linker between modules of a Type I PKS depending on the position of the module in the synthetic scheme for the polyketide. If the module is at the N-terminus of the polypeptide in which it resides—i.e., there is no additional module covalently bound upstream to it, an "interpolypeptide linker"(ERL) is placed upstream of the KS catalytic domain. Conversely, if the module resides in a polypeptide wherein there is an additional module upstream of it and covalently linked to it as a fusion protein, the two modules should be separated by an "intrapolypeptide linker" (RAL). If the module residing at the N-terminus of a polypeptide is downstream in the synthesis process for a polyketide—i.e., if it must accept a nascent polypeptide chain from a different module not on the same molecule, it may be necessary as well to supply a portion of the interpolypeptide linker at the C-terminus of the module providing the nascent polyketide chain in order to assure orderly transfer.

In the discussion that follows, polyketide synthases are discussed either at the protein level or the DNA level. As is well understood, manipulation of the sequence of amino acids in the polyketide synthase proteins is most conveniently done using recombinant techniques. Thus, for example, the appropriate linker sequences can be introduced to or modified with respect to those of an existing module by modifying the appropriate gene and expressing it in a suitable host. Interchange of linkers is also conveniently done in this manner. Further, modifications of amino acid sequences so as to obtain "variants" are effected by mutating the gene. The referent polyketide synthase should be understood to exist at both the protein level and nucleic acid level, and which form is being discussed should be apparent from the context.

Further, the action of polyketide synthases on their appropriate substrates can be effected either extracellularly by using isolated enzymes or may be effected by producing the enzymes intracellularly. By "appropriate substrate" is meant the extender units in their thioester forms that are recognized by the various modules in the PKS and "starter" units which are either thioesters of carboxylic acids or partially synthesize polyketides such as diketides. For example, as described in PCT application PCT/US96/11317, the ketosynthase domain of module 1 may conveniently be inactivated thus making more efficient the utilization of the diketide by module 2.

The linkers can be supplied by conventional recombinant DNA manipulations through the use of restriction enzymes and ligation procedures commonly practiced. The linkers in the PKS of the invention will be "isolated" from their natural environments. By "isolated," as used herein, is meant simply that the referent is found linked in association with moieties with which it is not normally associated, or in an environment in which it is not naturally found. It may be linked, if a nucleotide sequence to additional sequence with which it is not normally linked, or, if a peptide, to additional amino acid sequence with which it is not ordinarily linked, or it may be simply detached from additional moieties with which it is usually associated.

As seen from FIG. 3, the intrapeptide linkers (RAL) of the invention contain approximately 16–20 amino acid and typically contain a proline residue at approximately the middle of the sequence. On the other hand, the N-terminal upstream interpolypeptide linkers are approximately twice as long and appear to contain conserved acidic amino acid residues and basic amino acid residues at positions in the upstream half of the molecule. Thus, typical N-terminal upstream interpolypeptide linker (ERL) will contain an acidic amino acid within the first 3–10 residues, which is followed after 8–10 residues by a basic amino acid, and then after another 2–5 amino acid residues by an additional acidic amino acid. Additional acidic and basic residues may also occur in these linkers.

The intrapeptide linkers or interpeptide linkers shown in FIG. 3 can be used as described below in the present invention or the corresponding amino acid sequences from native Type I PKS in general can be employed. In addition to the sequences that occur in nature, "variants" may be used. These variants are obtained by altering the amino acid sequence of the linker in minor ways that do not affect the ability of the tinker to "feed" the nascent polyketide chain to the module in question. Typically, such "variants" are obtained from the native sequences by amino acid substitution, deletion or insertion; preferably the substitutions are "conservative" substitutions—i.e., an acidic amino acid for a different acidic amino acid, a basic amino acid for a different basic amino acid, and the like. Preferably, the variants contain no more than three amino acid alterations, preferably only two, and more preferably only one.

For construction of polyketide syntheses which contain more than one polypeptide, the appropriate sequence of transfers is assured by matching the appropriate C-terminal amino acid sequence of the donating module with the appropriate N-terminal amino acid sequence of the interpolypeptide linker of the accepting module. This can readily be done, for example, by selecting such pairs as they occur in native PKS. For example, two arbitrarily selected modules could be coupled using the C-terminal portion of module 4 of DEBS and the N-terminal of portion of the linking sequence for module 5 of DEBS.

In general, the method of the invention involves supplying to a module used in a PKS for synthesis of a desired polyketide with the appropriate N-terminal upstream portion interpolypeptide linker (N-ERL), C-terminal downstream portion of an interpolypeptide linker (C-ERL) or with an intrapolypeptide linker (RAL) at either terminus. As stated above, if the module is at the N-terminal portion of a polypeptide, an N-terminal upstream interpolypeptide linker should be appended at its N-terminus. If the module resides in a polypeptide where there is an additional module fused upstream from it, the two modules should be separated by an intrapolypeptide linker.

For ease of construction, a library of functional modules can be maintained to provide the appropriate desired module for construction of the PKS. One way to ensure the appropriate sequence of polyketide chain growth is to link the modules covalently, so that all but the first module will contain upstream intrapolypeptide linkers. Alternatively, and preferably, appropriate communication between functional modules non-covalently associated on separate polypeptide molecules can be achieved by providing appropriate matching between the C-terminal downstream portion of the interpolypeptide linker associated with the module contributing the nascent polyketide chain and the N-terminal upstream portion of the interpolypeptide linker placed upstream of the module which accepts and extends this nascent polyketide. Thus, an appropriate linker to ensure that the growing polyketide chain will be passed from module A to module B, which modules are not covalently bound, would be to couple, for example, the C-terminal scaffold portion of module 4 from erythromycin to module A and the N-terminal interpolypeptide linker (scaffold) portion from module 5 of the erythromycin PKS to the N-terminus of the KS of module B.

To design and construct the PKS, one straightforward approach is to utilize the existing linker regions of a native PKS, such as erythromycin PKS, and simply to "plug in" modules, for example from a library.

A library of modules derived from naturally occurring PKS which contains modules incorporating all alternative extender units used in native PKS combined with all variants of beta-carbonyl modification is not large. Extender units that are incorporated naturally include malonyl-CoA, methylmalonyl-CoA, ethylmalonyl-CoA, and hydroxymalonyl-CoA. The appropriate native molecule for incorporation of each of these can readily be found. Methylmalonyl-CoA extender units are incorporated, for example, by the modules of the erythromycin PKS. Certain modules of the picromycin PKS incorporate malonyl-CoA, while modules of the epothilone PKS incorporate ethylmalonyl-CoA or hydroxymalonyl-CoA. Modules occur naturally which contain the full spectrum of beta-carbonyl modifying activities; to the extent it is desirable to couple a particular beta-carbonyl modifying activity with a particular extender specificity, this can be accomplished by altering catalytic domains, per se, as described in the above-referenced PCT publication WO 98/49315. The complete combination of extender unit choices with all beta-carbonyl modification choices is thus only a total of 4×4 or 16 modules. As the KS unit determines the stereoselectivity of the module, accommodation can be made for various stereoisomeric forms of precursor by adjusting the KS domain in the module library. This expands the total number of modules necessary only to 32. An arbitrary number of modules can be included in a particular PKS construct, thus also determining the length of the polyketide chain and the size of the macrolide product. Of course, the macrolide product can be modified, if desired, by the known tailoring enzymes which convert naturally occurring macrolides to hydroxy- lated and/or glycosylated forms and the like. Such modification can be achieved in a variety of ways—by chemical modification, by in vitro treatruent with appropriate enzymes, or by feeding the polyketides to a host organism which contains the appropriate tailoring enzymes, as is well understood in the art.

To construct the desired PKS, modules are selected from the library and provided the appropriate upstream intrapolypeptide or interpolypeptide linkers. Suitable linkers can be selected from the group consisting of those shown in FIG. 3, the corresponding sequences from any Type I PKS, or can include variants of these depicted sequences which are conservative in nature and do not interfere with the ability of the linker to permit effective uptake of the nascent polypeptide chain. The linkers can be added by standard recombinant techniques to the modules in the library, or, the library can be composed of the collection of modules wherein each module has been further manipulated to include either an intrapolypeptide or interpolypeptide linker. It may be desirable, for example, to provide each type of extender module with an intrapolypeptide linker, including the possibility of retaining the linker that is normally associated with it. If the linker is placed at the N-terminus of the module, the module is suitable for covalent linking downstream of an additional module in a single polypeptide. If the intrapolypeptide linker is at the C-terminus, ordinarily that module will be placed and linked covalently upstream of an additional module. In any case, a module may arbitrarily be provided with an intrapolypeptide linker (RAL) at either its N- or C-termninus depending on where it is ultimately to be placed in the PKS to be constructed or may be provided with the N-terminal upstream portion of an interpolypeptide linker (N-ERL) if it is to be placed at the N-terminus of a polypeptide in the PKS, or with a C-terminal portion of an interpolypeptide linker (C-ERL) if it is to be pilaced at the C-terminus of a polypeptide and is intended to transfer a nascent polyketide chain to a subsequent module.

The various modules, with appropriate linkers are then assembled into the desired polyketide synthase. As stated above, the construction of the PKS can be based on plugging in active portions of modules into an existing linker array The assembly can be performed by simply mixing the peptides containing the modules or may be generated recombinantly from expression constructs in a host cell. The cell may piovide the appropriate substrates for the PKS, or the substrates may need to be provided to the reaction mixture containing the polypeptides or to the cells in which they are generated. Depending on the choice of host, provision may need to be made for providing these substrates.

In this way, the modules can be "mixed and matched" as desired to construct a polyketide product from the desired extender units and with the desired beta-carbonyl modification, choosing the linkers in accordance with the position of the module in a polypeptide, and the number of modules cam be altered as desired.

A preferred starter unit for such an assembly of modules is a diketide thioester either formed in situ by including a module which contains a loading domain to incorporate a starter unit along with an extender unit to attain this resultant, or the diketide may be synthesized independently and used as the substrate for the PKS. The synthesized diketide may be supplied as the thioester, such as the N-acylcysteamine thioesters. Preparation methods for these thioesters are described in the above-referenced U.S. Ser. No. 09/346,860 filed 2 Jul. 1999, now U.S. Pat. No. 6.221, 641, and the corresponding PCT application, as well as U.S. Ser. No. 09/492.733 filed 27 Jan. 2000, now U.S. Pat. No. 6,492,562 B1.

Using the techniques of the invention, it is thus possible to manipulate entire modules and effect efficient cross-talk so as to assure production of the desired macrolide. Such techniques can be used, for example, to alter the structure of macrolide anti-infectives by, for example, replacing the module 2 of the erythrom in gene cluster with module 2 of the tylosin gene cluster, or replacing the erythromycin module 6 (along with its thioester sequence) with the corresponding module 6 from narbomycin.

In addition, 14-membered macrolides could be expanded to become 16-membered macrolides by fusing modules 2–3 of the tylosin, spiramycin or niddamycin modules 2–3 between modules 1 and 3 of the erythromycin synthase or by adding any, arbitrarily chosen module from other Type I PKS clusters into the synthase for production of erythromycin. Alternatively, modules 1–2 of erythromycin could be deleted and replaced by modules 1–3 of tylosin, spiramycin or niddamycin.

In addition, new substituents can be introduced into, for example, PKS erythromycin or its precursors by replacing the second module of the erythromycin PKS with module 5 from tylosin PKS where the substituted module has the enoyl reductase catalytic activity inactivated. This results in erythromycins substituted with an ethyl group at the 10-position. Alternatively, erythromycin module 5 could be replaced by the spiramycin module 6 to obtain 5-desmethyl-4-OH erythromycins.

Improved forms of FK-506 are obtained by replacing rapamycin modules 2–10 with FK-506 modules 2–6, or by replacing rapamycin modules 2–11 with FK-506 modules 2–7 or by replacing rapamycin modules 2–12 with FK-506 modules 2–8 or by replacing rapamycin modules 11–14 with FK-506 modules 7–10. Any combination or subset of the above could also be employed. Improved forms of FK-520 can be made in a similar manner. An alternative form of rapamycin is synthesized by substituting the FK-506/520 module 1 for rapamycin module 1.

The foregoing are merely exemplary of the types of manipulations that could be employed. The polyketides, obtained by supplying the appropriate substrates either in vitro or in vivo, may then be further modified if desired by hydroxylation, glycosylation and the like to obtain desired products. Further, chemical synthetic manipulations may also be employed.

Some of the resulting compounds described above could be prepared by alternative techniques previously disclosed, for example, in PCT applications PCT/US99/22886 or PCT/US99/24483. However, the procedure described above, which manipulates entire modules, may result in better yield or more convenient synthesis.

The following examples are intended to illustrate but not to limit the invention.

PREPARATION A

Construction of Single Module Based Systems
Single Module Gene Constructs

Single module constructs from the DEBS gene cluster were prepared for modules 2, 3, 5 and 6 as follows. The TE domain is fused to the module to facilitate termination. The (M3+TE) gene was prepared from the tri-modular construct pKAO318 (McDaniel, R., et al., *Chem. Biol.* (1997) 4:667) having an NheI site engineered at the start of the DEBS-2 gene. Fusion of the TE gene at the end of ACP3 was described in connection with the construction of pCK13 in Cortes, J., et al., *Science* (1995) 268:1487; Kao, C. M., et al., *J. Am. Chem. Soc.* (1995) 117:9105 and Kao, C. M., et al., *J. Am. Chem.* Soc. (1996) 118:9184, collectively cited below as the "Cortes-Kao documents." The NheI-EcoRI fragment was cloned into pET 21c (Novagen) to construct pRSG34. The EcoRI site was used to delete the stop codon of the TE domain so that the protein could be overproduced as a carboxy terminal (His)6 tagged fusion protein.

(M5+TE) was constructed by combining the engineered NdeI site from pJRJ10 (Jacobsen, J. R., et al., *Biochem* (1998) 37:4928–4934) with the EcoRI site from pCK15 (Cortes-Kao, supra). The Nde-EcoRI fragment was cloned in pET21c to obtain the expression plasmid pRSG46. Expression constructs for (M2+TE) and (M6+TE) were prepared similarly using an engineered Nhe site immediately upstream of the corresponding KS (at position 7570, 5'-GCTAGCGAGCCGATC-3'(SEQ ID NO:1 )and at position 28710, 5'-GCTAGCGACCCGATC-3')(SEQ ID NO:2).

These constructs were expressed in *E. coli* BL21 (DE3) along with an expression system for sfp phosphopantetheinyl transferase from *B. subtilis*. The co-expression is described by Lambalot, R. H., et al, *Chem. Biol* (1996) 3:923. For the construction of the sfp gene, the NdeI-HindIII fragment derived from the pUC8-sfp (Nakano, M. M., et al., *Mol Gen. Genet*. (1992) 232:313–321) was cloned into pET28 which has a kanamycin resistance gene to give resultant plasmid pRSG56. The resulting proteins were then isolated for use in the reaction mixtures described in the Examples below.

In more detail, the expression was induced with 1 mM isopropyl-b-D-thiogalactopyranoside, and the cells were harvested by centrifugation after 10 hours and resuspended in disruption buffer, 200 mM sodium phosphate pH 7.2, 200 mM sodium chloride, 2.5 mM dithiothreitol, 2.5 mM sodium ethylenediamine tetraacetate (EDTA), 1.5 mM benzamidine, 2 mg/L pepstatin and leupeptin and 30% v/v glycerol. The cells were lysed by passing through a french press, and the lysate was collected after centrifugation. Nucleic acids were precipitated with polyethylenimine (0.15%) and removed via centrifugation. The supernatant was made 50%(w/v) saturated with ammonium sulfate and precipitated overnight. After centrifugation, the pellet containing protein was redissolved in buffer A (100 mM sodium phosphate pH 7.2, 2.5 mM DTT, 2 mM EDTA and 20% glycerol (v/v)) and stored at −80° C. For chromatography, the buffer was exchanged to buffer A+1 M ammonium sulfate using a gel filtration PD 10 (Pharmacia) column. The resulting sample was loaded on a Butyl Sepharose (Phannacia) column. Fractions containing DEBS proteins were pooled and applied on an anion exchange column (Resource Q; 6 mL, Pharmacia). Purifled protein fractions were pooled and concentrated using Amicon centriprep30. Typical purified protein yields were~3–4 mg/liter of culture. Greater than 90% of proteins were phosphopantetheinylated in vivo as a result of the overexpression of sfp phosphopantetheinyl transferase. Although the proteins were expressed as $(HiS)_6$-tagged proteins, they did not bind to a Ni-column under experimental conditions. It is unclear whether this inability to bind to a Ni-agarose column is due to steric effects or if the $(HiS)_6$ peptide was lost during purification.

EXAMPLE 1

Figure 2:
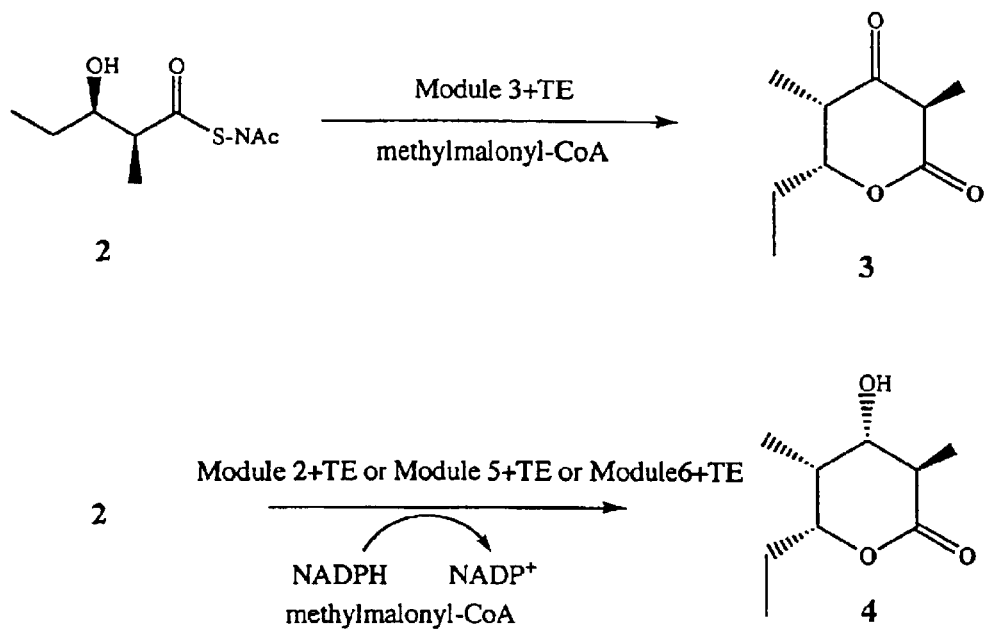
FIG. 2 shows the conversion of a diketide thioester to the triketides corresponding to those produced by DEBS-1 of the erythromycin PKS.

Requirements for Cell-Free Synithesis of Triketides by Individual Modules—Identification of Linker Regions A cell-free system, tested for the ability to convert the cysteamine thioester of 2S,3R-2-methyl-3- hydroxypentanoic acid (compound 2 in FIG. 2), consisted of 0.5–10 mM concentration of the thioester, 2.5 mM $^{14}$C-labeled methylmalonyl CoA and 100 pmoles of purified protein prepared in Example 1 in a 100 μl reaction. In some cases, 1 mM of NADPH was added; this was done in assay mixtures containing (M2+TE), (M5+TE) and (M6+TE) proteins. The protein was, in each case, a single module of the DEBS PKS fused to the thioesterase (TE) termination region of module 6.

The reaction mixtures were quenched and extracted by ethyl acetate and separated by thin-layer chromatography (TLC) to discern the formation of the triketides ketolactone 3 and triketides lactone 4 (both shown in FIG. 2) after 30 minutes. Results are shown as the first four entries in Table 1.

TABLE 1

Formation of Triketides by Single Module Constructs

| Construct | Plasmid | Triketide Formed |
|---|---|---|
| 1. M3 + TE | pRSG34 | Yes |
| 2. M5 + TE | pRSG46 | Yes |
| 3. M2 + TE | — | No |
| 4. M6 + TE | — | No |
| 5. ERL – M2 + TE | pRSG64 | Yes |
| 6. ERL – M6 + TE | pRSG54 | Yes |
| 7. M1 – RAL – M6 – TE | pST96 | Yes |
| 8. M1 – RAL – M3 – TE | pST97 | Yes |
| 9. ery M1 – RAL – rif M5 + TE | pST110 | Yes |
| 10. (ery M1 – RAL rif M5 + ERL) + DEBS – 2 + DEBS – 3 | pST113 | Yes (dEB6) |

As seen in Table 1, although the expected triketides were formed from (M3+TE) and (M5+TE) (modules which reside at the upstream portion of their respective polypeptides), no triketides were formed from (M2+TE) or (M6+TE), (modules which reside at the C-terrninal portions of their polypeptides). These latter results were unexpected since the diketide can be incorporated by module 2 when it is supplied as a part of the complete polypeptide DEBS-1. It was verified that the ACP domain was pantetheinylated in modules 2 and 6, and that for (M2+TE), the KS domain could not be acylated with radiolabeled diketide.

EXAMPLE 2

Modification of Single Modules with Linker Sequences

The constructs for (M2+TE) and (M6+TE) were modified by deleting the sequences encoding the amino acids upstream of the KS catalytic domain and substituting the first 39 amino acids from (M5+TE) containing the N-terminal portion of the interpolypeptide linker (N-ERL). The relevant constructs were prepared by replacing the BsaBI-EcoRI fragment in pRSG46 by the corresponding fragment from pCK4 to obtain (N-ERL-M2+TE), in plasmid pRSG64, or from pJRJ10 to obtain (N-ERL-M6+TE) in plasmid pRSG54. These constructs yield modules which contain the upstream 39 amino acids from module 5. The constructs were expressed in E. coli and proteins obtained as described in Preparation A. These proteins were able to produce the triketides product from diketide in the cell free system of Example 1, as shown in entries 5 and 6 in Table 1.

The various constructs which are successful in converting diketide to triketides were then evaluated for the kinetic constants $k_{cat}$ and $K_M$. These results are shown in Table 2. As shown in Table 2, the results are quite similar for all constructs except that the results from module 3 show a several-fold decrease in $k_{cat}$ as compared to the other modules. This is evidently due to the absence of beta-carbonyl modifying enzymes in module 3 as verified by the fact that removal of NADPH, (which is required for the activity of such modules) from the reaction mixture of (N-ERL-M6+TE) also results in a lowering of the $k_{cat}$.

TABLE 2

| Proteins | $k_{cat}$ X 100 (min$^{-1}$) | $K_M$ (mM) |
|---|---|---|
| (N – ERL – M2 + TE) | 8 ± 0.6 | 4.6 ± 0.4 |
| (M3 + TE) | 1.5 ± 0.3 | 4.4 ± 0.4 |
| (M5 + TE) | 7.5 ± 0.7 | 4.7 ± 0.4 |
| (N – ERL – M6 + TE) | 9.5 ± 0.6 | 4.3 ± 0.4 |
| (N – ERL – M6 + TE) (–NADPH) | 4.5 ± 0.7 | 4.1 ± 0.4 |

It is apparent from these results that the presence of the N-terminal upstream sequence associated with modules located at the N-terminal portion of the polypeptide is essential for permitting a module in this position to incorporate the growing polyketide chain.

EXAMPLE 3

Construction of (M1-RAL-M3+TE) and (M1-RAL-M6+TE)

The BsaBI-EcoRI fragments containing modules 3 and 6 respectively were cloned behind the M1 module which contains the intrapolypeptide linker (RAL) that natively resides between M1 and M2. The resulting M1-RAL-M3+TE and M1-RkL-M6+TE genes were then excised as PacI-EcoRI fragments and inserted into pCK 12 resulting plasmids pST97 and pST96 respectively. The corresponding proteins were produced by transformation into S. coelicolor CH999. The resulting strains of S. coelicolor were able to incorporate the diketide thioester into the triketides as shown by entries.7 and 8 in Table 1. (The triketides produced is the ketolactone 3 in FIG. 2.)

EXAMPLE 4

Additional Intrapolypeptide Mediated Transfer

A construct wherein the first module of the DEBS PKS cluster (ery), which contains the intrapolypeptide linker of the corresponding M1-M2 polypeptide from the erythromycin PKS, is fused to the fifth module of the rifamycin PKS (rif) was constructed by replacing the natural sequence at 28024 of rif ACP5 (5'-CGCGAC-3') with the SpeI recognition sequence 5'-ACTAGT-3'. The BsaBI-SpeI fragment containing rif M5 was excised and replaced the corresponding ery M1-RAL- fragment in pCK12 to obtain plasmid pST 110. This plasmid, containing ery M1-RAL-rif-M5+TE was transformed into S. coelicolor CH999 and the resulting strain was able to incorporate the diketide into the triketides lactone as shown by entry 9 in Table 1. The amount is comparable to that produced in this strain transformed with DEBS-1+TE.

EXAMPLE 5

Construction of Modules for Intermolecular Transfer

The PacI-SpeI fragment of pST110 was inserted into a derivative of pCK7 (Kao, C. M., et al., Science (1994) 265:509) which had an SpeI site engineered at the beginning of the scaffolding sequence at the carboxy terminus of the polypeptide downstream of ACP2. The resulting pST 113 construct still contains ery M1 linked to rifM5 via the natural intrapolypeptide linker between ery molecules 1 and 2, and also now contains rifM5 covalently linked to the downstream C-terminal portion of the ERL derived from ery M2. Thus, the complete ERL between the polypeptide generated by pST113 and the protein generated by a construct which generates DEBS-2 would correspond to the native ERL in polypeptide downstream of ACP2. The resulting pST 113 the ery PKS—i.e., rifM5 would be associated with ery M3 via the natural interpolypeptide linker between ery molecules 2 and 3. Co-transformation into *S. coelicolor* of pST 113 along with constructs that produce DEBS-2 and DEBS-3 results in the production of 6-dEB, as shown by entry 10 of Table 1.

What is claimed is:

1. A hybrid modular polyketide synthase (PKS) comprising at least a first extender module and a second extender module of a different PKS from said first module,
   wherein said extender modules are defined as consisting of the amino acid sequence from the N-terminus of the ketosynthase (KS) domain through the C-terminus of the acyl transferase protein (ACP) domain:
   wherein the C-terminus of said first module is covalently linked to the N-terminus of a intramolecular linker (RAL) and the N-terminus of the second module is covalently linked to the C-terminus of said RAL, and
   wherein said RAL is defined as the amino acid sequence between the C-terminus of an upstream ACP domain and the N-terminus of an adjacent downstream KS domain; said ACP and KS domains occupying adjacent modules in the same reading frame;
   wherein either said first module or second module is not covalently linked to said RAL in a naturally occurring polyketide synthase;
   whereby the RAL effects the transfer of a nascent polyketide chain from said first module to said second module.

2. The hybrid modular PKS of claim 1 wherein said RAL is selected from the group consisting of M2 ery, M4 ery, M6 ery, M2 rif, M3 rif, M5 rif, M3 rap, M4 rap, and M7 rap intra-module linkers (SEQ. ID. NO's: 3–11, respectively).

3. The hybrid modular PKS of claim 1 which contains ery modules 1 and 3 through 6 inclusive and tylosin module 2, and wherein said polyketide chain is transferred from ery module 1 to ery module 2 and then to ery modules 3 through 6 inclusive.

4. The hybrid modular PKS of claim 1 which contains ery modules 1 through 5 inclusive and narbomycin module 6, wherein said polyketide chain is transferred from ery modules 1 through 5 inclusive to nar module 6.

5. The hybrid modular PKS of claim 1 which contains modules 1 and 3 through 6 inclusive of ery and modules 2–3 of tylosin, spiramycin or niddamycin, wherein said polyketide chain is transferred from ery module 1 to modules 2–3 of tylosin, spiramycin or niddamycin and then to ery modules 3 through 6 inclusive.

6. The hybrid modular PKS of claim 1 which contains modules 1 through 3 inclusive of tylosin, spiramycin or niddamycin and modules 3 through 6 inclusive of ery, and wherein said polyketide chain is transferred from modules 1 through 3 inclusive of said tylosin, spiramycin or niddamycin to ery modules 3 through 6 inclusive.

7. The hybrid modular PKS of claim 1 which contains a module of tylosin, spiramycin or niddamycin and modules 1–2 and 3 through 6 inclusive of ery, wherein said polyketide chain is transferred from ery modules 1–2 to the tylosin, spiramycin or niddamycin module and then to ery modules 3 through 6 inclusive.

8. The hybrid modular PKS of claim 1 which contains modules 1 and 3 through 6 inclusive of ery and module 5 of tylosin, spiramycin or niddamycin having the enoyl reductase catalytic activity inactivated, wherein said polyketide chain is transferred from ery module 1 to module 5 of tylosin, spiramycin or niddamycin and then to ery modules 3 through 6 inclusive.

9. The hybrid modular PKS of claim 1 which contains ery modules 1 through 4 inclusive and 6 and module 6 of spiramycin or niddamycin, wherein said polyketide chain is transferred from ery modules 1 through 4 inclusive to ery module 6 of spiramycin or niddamycin and then to ery module 6.

10. The hybrid modular PKS of claim 1 which contains module 1 of FK-506 or 520 and modules 2 through 14 inclusive of rapamycin, wherein said polyketide chain is transferred from module 1 of FK-506 or 520 and then to modules 2 through 14 inclusive of rapamycin.

11. The hybrid modular PKS of claim 1 which contains module 1 and 11 through 14 inclusive of rapamycin and modules 2 through 6 inclusive of FK-506 or 520 wherein said polyketide chain is transferred from module 1 of rapamycin to modules 2 through 6 inclusive of FK-506 or 520 and then to modules 11 through 14 inclusive of rapamycin.

12. The hybrid modular PKS of claim 1 which contains module 1 of rapamycin, modules 2 through 7 inclusive of FK-506 or 520 and modules 12 through 14 inclusive of rapamycin, wherein said polyketide chain is transferred from module 1 of rapamycin to modules 2 through 7 inclusive of FK-506 or 520 and then to modules 12 through 14 inclusive of rapamycin.

13. The hybrid modular PKS of claim 1 which contains module 1 of rapamycin, modules 2 through 8 inclusive of FK-506 or 520 and modules 13–14 of rapamycin, wherein said polyketide chain is transferred from module 1 of rapamycin to modules 2 through 8 inclusive of FK-506 or 520 and then to modules 13–14 of rapamycin.

14. The hybrid modular PKS of claim 1 which contains modules 1 through 10 inclusive of rapamycin and modules 7 through 10 inclusive of FK-506 or 520, wherein said polyketide chain is transferred from modules 1 through 10 inclusive of rapamycin to modules 7 through 10 inclusive of FK-506 or 520.

15. A hybrid modular polyketide synthase (PKS) comprising at least a first extender module and a second extender module of a different PKS from said first module,
   wherein said extender modules are defined as consisting of the amino acid, sequence from the N-terminus of the ketosynthase (KS) domain through the C-terminus of the acyl transferase protein (ACP) domain:
   wherein the C-terminus of said first module is covalently linked to the N-terminus of a intermolecular linker (ERL) and the N-terminus of the second module is covalently linked to the C-terminus of said ERL, and
   wherein said ERL is defined as a contiguous polypeptide comprising, in order, (1) the amino acid sequence beginning at the C-terminus of the ACP domain of the most downstream module of a first open reading frame and (2) the amino acid sequence upstream of the N-terminus of the most upstream KS domain of a second open reading frame, which second open reading frame is immediately adjacent to and downstream of said first open reading frame; and
   wherein either said first module or second module is not covalently linked to said ERL in a naturally occurring polyketide synthase;
   whereby the ERL effects the transfer of a nascent polyketide chain from said first module to said second module.

16. The hybrid modular PKS of claim 15 wherein the portion of the ERL at the N-terminus of the second module is selected from the group consisting of SEQ. ID. NO's: 12–19, respectively.

17. The hybrid modular PKS of claim 15 which contains ery modules 1 and 3 through 6 inclusive and tylosin module 2, and wherein said polyketide chain is transferred from ery module 1 to tyl module 2 and then to ery modules 3 through 6 inclusive.

18. The hybrid modular PKS of claim 15 which contains ery modules 1 through 5 inclusive and narbomycin module 6, wherein said polyketide chain is transferred from ery modules 1 through 5 inclusive to nar module 6.

19. The hybrid modular PKS of claim 15 which contains modules 1 and 3 through 6 inclusive of ery and modules 2–3 of tylosin, spiramycin or niddamnycin, wherein said polyketide chain is transferred from ery module 1 to modules 2–3 of tylosin, spiramycin or niddamycin and then to ery modules 3 through 6 inclusive.

20. The hybrid modular PKS of claim 15 which contains modules 1 through 3 inclusive of tylosin, spiramycin or niddamycin and modules 3 through 6 inclusive of ery, and wherein said polyketide chain is transferred from modules 1 through 3 inclusive of tylosin, spiramycin or niddamycin to ery modules 3 through 6 inclusive.

21. The hybrid modular PKS of claim 15 which contains a module of tylosin, spiramycin or niddamycin and modules 1–2 and 3 through 6 inclusive of ery, wherein said polyketide chain is transferred from ery modules 1–2 to the tylosin, spiramycin or niddamycin module and then to ery modules 3 through 6 inclusive.

22. The hybrid modular PKS of claim 15 which contains modules 1 and 3 through 6 inclusive of ery and module 5 of tylosin, spiramycin or niddamycin having the enoyl reductase catalytic activity inactivated, wherein said polyketide chain is transferred from ery module 1 to module 5 of tylosin, spiramycin or niddamycin and then to ery modules 3 through 6 inclusive.

23. The hybrid modular PKS of claim 15 which contains ery modules 1 through 4 inclusive and 6 and module 6 of spiramycin or niddamycin, wherein said polyketide chain is transferred from ery modules 1 through 4 inclusive to module 6 of spiramycin or niddamycin and then to ery module 6.

24. The hybrid modular PKS of claim 15 which contains module 1 of FK-506 or 520 and modules 2 through 14 inclusive of rapamycin, wherein said polyketide chain is transferred from module 1 of FK-506 or 520 and then to modules 2 through 14 inclusive of rapamycin.

25. The hybrid modular PKS of claim 15 which contains module 1 and 11 through 14 inclusive of rapamycin and modules 2 through 6 inclusive of FK-506 or 520 wherein said polyketide chain is transferred from module 1 of rapamycin to modules 2 through 6 inclusive of FK-506 or 520 and then to modules 11 through 14 inclusive of rapamycin.

26. The hybrid modular PKS of claim 15 which contains module 1 of rapamycin, modules 2 through 7 inclusive of FK-506 or 520 and modules 12 through 14 inclusive of rapamycin, wherein said polyketide chain is transferred from module 1 of rapamycin to modules 2 through 7 inclusive of FK-506 or 520 and then to modules 12 through 14 inclusive of rapamycin.

27. The hybrid modular PKS of claim 15 which contains module 1 of rapamycin, modules 2 through 8 inclusive of FK-506 or 520 and modules 13–14 of rapamycin, wherein said polyketide chain is transferred from module 1 of rapamycin to modules 2 through 8 inclusive of FK-506 or 520 and then to modules 13–14 of rapamycin.

28. The hybrid modular PKS of claim 15 which contains modules 1 through 10 inclusive of rapamycin and modules 7 through 10 inclusive of FK-506 or 520, wherein said polyketide chain is transferred from modules 1 through 10 inclusive of rapamycin to modules 7 through 10 inclusive of FK-506 or 520.

\* \* \* \* \*

SEQUENCE LISTING

```
<160> NUMBER OF SEQ ID NOS: 19

<210> SEQ ID NO 1
<211> LENGTH: 15
<212> TYPE: DNA
<213> ORGANISM: Artificial Sequence
<220> FEATURE:
<223> OTHER INFORMATION: Engineered Nhe site of the corresponding KS (at
      position 7570)

<400> SEQUENCE: 1
gctagcgagc cgatc                                                    15

<210> SEQ ID NO 2
<211> LENGTH: 15
<212> TYPE: DNA
<213> ORGANISM: Artificial Sequence
<220> FEATURE:
<223> OTHER INFORMATION: Engineered Nhe site of the corresponding KS (at
      position 28710)

<400> SEQUENCE: 2
gctagcgacc cgatc                                                    15

<210> SEQ ID NO 3
<211> LENGTH: 18
<212> TYPE: PRT
<213> ORGANISM: Artificial Sequence
<220> FEATURE:
<223> OTHER INFORMATION: Intra-polypeptide linker M2ery

<400> SEQUENCE: 3

Gly Gly Ala Thr Gly Ala Glu Gln Ala Ala Pro Ala Thr Thr Ala Pro
 1               5                  10                  15

Val Asp

<210> SEQ ID NO 4
<211> LENGTH: 18
<212> TYPE: PRT
<213> ORGANISM: Artificial Sequence
<220> FEATURE:
<223> OTHER INFORMATION: Intra-polypeptide linker M4ery

<400> SEQUENCE: 4

Val Gly Asp Ala Asp Gln Ala Ala Val Arg Val Val Gly Ala Ala Asp
 1               5                  10                  15

Glu Ser

<210> SEQ ID NO 5
<211> LENGTH: 21
<212> TYPE: PRT
<213> ORGANISM: Artificial Sequence
<220> FEATURE:
<223> OTHER INFORMATION: Intra-polypeptide linker M6ery

<400> SEQUENCE: 5
```

```
Val Gly Ala Ala Glu Ala Glu Gln Ala Pro Ala Leu Val Arg Glu Val
  1               5                  10                 15

Pro Lys Asp Ala Asp
            20

<210> SEQ ID NO 6
<211> LENGTH: 17
<212> TYPE: PRT
<213> ORGANISM: Artificial Sequence
<220> FEATURE:
<223> OTHER INFORMATION: Intra-polypeptide linker M2rif

<400> SEQUENCE: 6

Phe Gly Ser Ala Ala Asn Arg Pro Ala Glu Ile Gly Thr Ala Ala Ala
  1               5                  10                 15

Glu

<210> SEQ ID NO 7
<211> LENGTH: 17
<212> TYPE: PRT
<213> ORGANISM: Artificial Sequence
<220> FEATURE:
<223> OTHER INFORMATION: Intra-polypeptide linker M3rif

<400> SEQUENCE: 7

Leu Gly Glu Arg Pro Ala Ala Pro Ala Pro Val Thr Arg Asp Val Ser
  1               5                  10                 15

Asp

<210> SEQ ID NO 8
<211> LENGTH: 19
<212> TYPE: PRT
<213> ORGANISM: Artificial Sequence
<220> FEATURE:
<223> OTHER INFORMATION: Intra-polypeptide linker M5rif

<400> SEQUENCE: 8

Gly Glu Thr Val Ala Gly Ala Pro Ala Thr Pro Val Thr Thr Val Ala
  1               5                  10                 15

Asp Ala Gly

<210> SEQ ID NO 9
<211> LENGTH: 21
<212> TYPE: PRT
<213> ORGANISM: Artificial Sequence
<220> FEATURE:
<223> OTHER INFORMATION: Intra-polypeptide linker M3rap

<400> SEQUENCE: 9

Glu Leu Phe Thr Gly Glu Asn Pro Ala Pro Val Arg Gly Pro Val Ser
  1               5                  10                 15

Ala Val Gly Gln Asp
            20

<210> SEQ ID NO 10
<211> LENGTH: 21
<212> TYPE: PRT
<213> ORGANISM: Artificial Sequence
<220> FEATURE:
<223> OTHER INFORMATION: Intra-polypeptide linker M4rap

<400> SEQUENCE: 10

Glu Leu Phe Thr Gly Glu Asn Pro Ala Pro Val Arg Gly Pro Val Ser
```

```
                1               5              10              15
Val Val Gly Gln Asp
                20

<210> SEQ ID NO 11
<211> LENGTH: 20
<212> TYPE: PRT
<213> ORGANISM: Artificial Sequence
<220> FEATURE:
<223> OTHER INFORMATION: Intra-polypeptide linker M7rap

<400> SEQUENCE: 11

Glu Leu Phe Thr Gly Glu Asn Pro Ala Pro Val Arg Gly Pro Val Ser
1               5                   10                  15

Ala Gly Gln Asp
            20

<210> SEQ ID NO 12
<211> LENGTH: 30
<212> TYPE: PRT
<213> ORGANISM: Artificial Sequence
<220> FEATURE:
<223> OTHER INFORMATION: N-terminal inter-polypeptide linker M3ery

<400> SEQUENCE: 12

Val Thr Asp Ser Glu Lys Val Ala Glu Tyr Leu Arg Arg Ala Thr Leu
1               5                   10                  15

Asp Leu Arg Ala Ala Arg Gln Arg Ile Arg Glu Leu Glu Ser
            20                  25                  30

<210> SEQ ID NO 13
<211> LENGTH: 38
<212> TYPE: PRT
<213> ORGANISM: Artificial Sequence
<220> FEATURE:
<223> OTHER INFORMATION: N-terminal inter-polypeptide linker M5ery

<400> SEQUENCE: 13

Met Ser Gly Asp Asn Gly Met Thr Glu Glu Lys Leu Arg Arg Tyr Leu
1               5                   10                  15

Lys Arg Thr Val Thr Glu Leu Asp Ser Val Thr Ala Arg Leu Arg Glu
            20                  25                  30

Val Glu His Arg Ala Gly
            35

<210> SEQ ID NO 14
<211> LENGTH: 34
<212> TYPE: PRT
<213> ORGANISM: Artificial Sequence
<220> FEATURE:
<223> OTHER INFORMATION: N-terminal inter-polypeptide linker M4rif

<400> SEQUENCE: 14

Met Ser Ala Pro Asn Glu Gln Ile Val Asp Ala Leu Arg Ala Ser Leu
1               5                   10                  15

Lys Glu Asn Val Arg Leu Gln Gln Glu Asn Ser Ala Leu Ala Ala Ala
            20                  25                  30

Ala Ala

<210> SEQ ID NO 15
<211> LENGTH: 34
<212> TYPE: PRT
<213> ORGANISM: Artificial Sequence
```

-continued

```
<220> FEATURE:
<223> OTHER INFORMATION: N-terminal inter-polypeptide linker M7rif

<400> SEQUENCE: 15

Val Ser Ala Ser Tyr Glu Lys Val Val Glu Ala Leu Arg Lys Ser Leu
 1               5                  10                  15

Glu Glu Val Gly Thr Leu Lys Lys Arg Asn Arg Gln Leu Ala Asp Ala
            20                  25                  30

Ala Gly

<210> SEQ ID NO 16
<211> LENGTH: 32
<212> TYPE: PRT
<213> ORGANISM: Artificial Sequence
<220> FEATURE:
<223> OTHER INFORMATION: N-terminal inter-polypeptide linker M8rif

<400> SEQUENCE: 16

Val Ala Asp Glu Gly Gln Leu Arg Asp Tyr Leu Lys Arg Ala Ile Ala
 1               5                  10                  15

Asp Ala Asp Ala Arg Thr Arg Leu Arg Glu Val Glu Glu Gln Ala Arg
            20                  25                  30

<210> SEQ ID NO 17
<211> LENGTH: 30
<212> TYPE: PRT
<213> ORGANISM: Artificial Sequence
<220> FEATURE:
<223> OTHER INFORMATION: N-terminal inter-polypeptide linker M9rif

<400> SEQUENCE: 17

Met Ala Thr Asp Glu Lys Leu Leu Lys Tyr Leu Lys Arg Val Thr Ala
 1               5                  10                  15

Glu Leu His Ser Leu Arg Lys Gln Gly Ala Arg His Ala Asp
            20                  25                  30

<210> SEQ ID NO 18
<211> LENGTH: 32
<212> TYPE: PRT
<213> ORGANISM: Artificial Sequence
<220> FEATURE:
<223> OTHER INFORMATION: N-terminal inter-polypeptide linker M5rap

<400> SEQUENCE: 18

Met Arg Glu Asp Gln Leu Leu Asp Ala Leu Arg Lys Ser Val Lys Glu
 1               5                  10                  15

Asn Ala Arg Leu Arg Lys Ala Asn Thr Ser Leu Arg Ala Ala Met Asp
            20                  25                  30

<210> SEQ ID NO 19
<211> LENGTH: 33
<212> TYPE: PRT
<213> ORGANISM: Artificial Sequence
<220> FEATURE:
<223> OTHER INFORMATION: N-terminal inter-polypeptide linker M11rap

<400> SEQUENCE: 19

Met Pro Glu Gln Asp Lys Val Val Glu Tyr Leu Arg Trp Ala Thr Ala
 1               5                  10                  15

Glu Leu His Thr Thr Arg Ala Lys Leu Glu Ala Leu Ala Ala Ala Asn
            20                  25                  30

Thr
```